United States Patent [19]

Carpenter

[11] Patent Number: 4,692,144
[45] Date of Patent: Sep. 8, 1987

[54] SYSTEM FOR PROVIDING INTRAVENOUSLY ADMINISTRABLE DRUG FORMULATION

[75] Inventor: Peter F. Carpenter, Atherton, Calif.

[73] Assignee: ALZA Corporation, Palo Alto, Calif.

[21] Appl. No.: 848,242

[22] Filed: Apr. 4, 1986

Related U.S. Application Data

[63] Continuation of Ser. No. 642,233, Aug. 20, 1984, abandoned.

[51] Int. Cl.$^4$ .............................................. A61M 5/00
[52] U.S. Cl. .................................... 604/56; 604/80; 604/85
[58] Field of Search ......................... 604/56, 80–86, 604/92, 246

[56] References Cited

U.S. PATENT DOCUMENTS

| | | | |
|---|---|---|---|
| 2,656,837 | 10/1953 | Bryan | 604/78 |
| 2,690,179 | 9/1954 | Fox | 604/87 |
| 3,120,125 | 2/1964 | Vasel | 73/293 |
| 3,941,126 | 3/1976 | Dietrich et al. | 604/80 |
| 3,949,744 | 4/1976 | Clarke | 604/246 |
| 4,193,004 | 3/1980 | Lobdell et al. | 250/577 |
| 4,343,316 | 8/1982 | Jepersen | 128/771 |
| 4,355,238 | 10/1982 | Ruell | 250/577 |
| 4,424,056 | 1/1984 | Urquhart | 604/85 X |
| 4,448,207 | 5/1984 | Parrish | 128/771 |
| 4,450,722 | 5/1984 | Keyes et al. | 73/293 |
| 4,465,471 | 8/1984 | Harris et al. | 604/56 |
| 4,522,622 | 6/1985 | Peery et al. | 604/191 |

Primary Examiner—Dalton L. Truluck
Attorney, Agent, or Firm—Paul L. Sabatine; Edward L. Mandell; Steven F. Stone

[57] ABSTRACT

An intravenous delivery system is disclosed for formulating an intravenously administrable solution in the delivery system. The delivery system comprises means for transferring a fluid and for mixing the fluid with a drug in the delivery system.

6 Claims, 10 Drawing Figures

SYSTEM FOR PROVIDING INTRAVENOUSLY ADMINISTRABLE DRUG FORMULATION

CROSS-REFERENCE TO RELATED APPLICATION

This application is a continuation of U.S. Ser. No. 06/642,233 filed Aug. 20, 1984 now abandoned.

FIELD OF THE INVENTION

This invention pertains to a system for (a) formulating a fluid drug formulation, and for (b) delivering the fluid drug formulation intravenously to a host. The system comprises (1) a fluid container of an intravenously administrable fluid, (2) a drug container containing initially a drug or a means for providing a drug, (3) means for conveying fluid from the fluid container to the drug container for forming a fluid drug formulation in the container, and (4) means for intravenously administering the fluid drug formulation to a recipient.

BACKGROUND OF THE INVENTION

The intravenous administration of fluids is an established clinical practice. The clinical practice of administering fluids is used extensively as an integral part of the daily treatment of medical and surgical patients. The fluids administered intravenously usually include aqueous solutions of dextrose, sodium chloride and solutions of various other electrolytes. Generally, the fluids are administered from a container that is suspended above a patient, with the fluid flowing from the container through an administration set and thence to a catheter or a hypodermic needle placed in a blood vessel, usually a vein of a patient.

The administration of fluids intravenously is a valuable and important component of patient care; moreover, the use of intravenous fluids in recent years has expanded beyond its original role of fluid and electrolyte replacement to include serving as the vehicle for the intravenous administration of beneficial drugs, notably those which are desirable to administer by infusion via the intravenous route. For example, presently a beneficial drug is administered intravenously by one of the following procedures: (1) temporarily halting the flow of medical fluid and intravenously administering the drug, followed by resumption of medical fluid into the patient; (2) the drug is added to the fluid in a container and then carried by the flow of fluid to the patient; (3) a drug is introduced into a so-called "piggyback" container, which is subsequently connected to a primary line through which the drug is administered to a patient, or (4) the drug is administered by a pump that exerts a force on a fluid containing a drug for intravenously administering the fluid containing the drug.

While these delivery techniques are used, they have certain disadvantages associated with their use. For example, they often require performulation of the drug with the medical fluid by the hospital pharmicist or the nurse, and this frequently requires storing the premixed formulation at a lower temperature to prevent degradation of the formulation. Also, beneficial drugs that are fluid sensitive and require formulation with a fluid at the time of administration presently cannot be administered by these prior art systems. Additionally, the prior art systems often require separate connections for joining into the intravenous line that further complicates intravenous administration, and the use of pumps can produce pressures that can vary at the delivery site and the pump pressure can give rise to thrombosis.

DISCLOSURE OF THE INVENTION

A principle object of this invention is to provide both a novel and useful intravenous delivery system that overcomes the disadvantages associated with the prior art, and which present delivery system is an improved delivery system for intravenous drug administration.

Another object of the present invention is to provide an intravenous delivery system comprising means for the in situ, self-formulation of a fluid drug formulation for administering to a patient whose prognosis benefits from intravenous drug administration.

Another object of the invention is to provide an intravenous delivery system comprising initially a drug and a means for adding a medical fluid to the drug for forming a fluid drug formulation for administering to a patient at the time it is prepared for optimizing the care of the patient.

Another object of this invention is to provide an intravenous delivery system originally containing a drug and a means for automatically constituting a drug formulation in situ by dissolving a given amount of drug in a given volume of a fluid that can be administered at any preselected time to a patient on intravenous therapy.

Another object of the present invention is to provide an intravenous delivery system that is self-contained and makes attainable a program of drug administration adapted to a specific need by furnishing a fluid drug formulation formed in situ by mixing a known volume of fluid with from a trace to a saturating amount of a beneficial drug.

Another object of the present invention is to provide an intravenous delivery system comprising initially a drug free of fluid to which drug fluid can be added as needed for forming a fluid drug formulation acceptable for intravenous therapy.

Another object of the invention is to provide an intravenous delivery system that is easy to manufacture, is inexpensive, is easy to operate, and provides instant drug formulation and delivery to a needy patient.

Another object of the invention is to provide an intravenous delivery system that can administer a drug in solution at a controlled and continuous rate to a human for a particular time period, the use of which requires intervention only for initiation and termination of the delivery.

Other objects, feature, aspects and advantages of the invention will be more apparent to those versed in the art from the following detailed specification taken in conjunction with the drawing figures and the accompanying claims.

BRIEF DESCRIPTION OF THE DRAWINGS

In the drawings, which are not drawn to scale, but are set forth to illustrate various embodiments of the invention, the drawing figures are as follows.

In the specification and the drawing, like parts in related figures are identified by like numbers. The terms appearing earlier in the specification and in the description of the drawing figures are disclosed hereinafter in this disclosure.

DETAILED DESCRIPTION OF THE DRAWINGS

Figure 1:
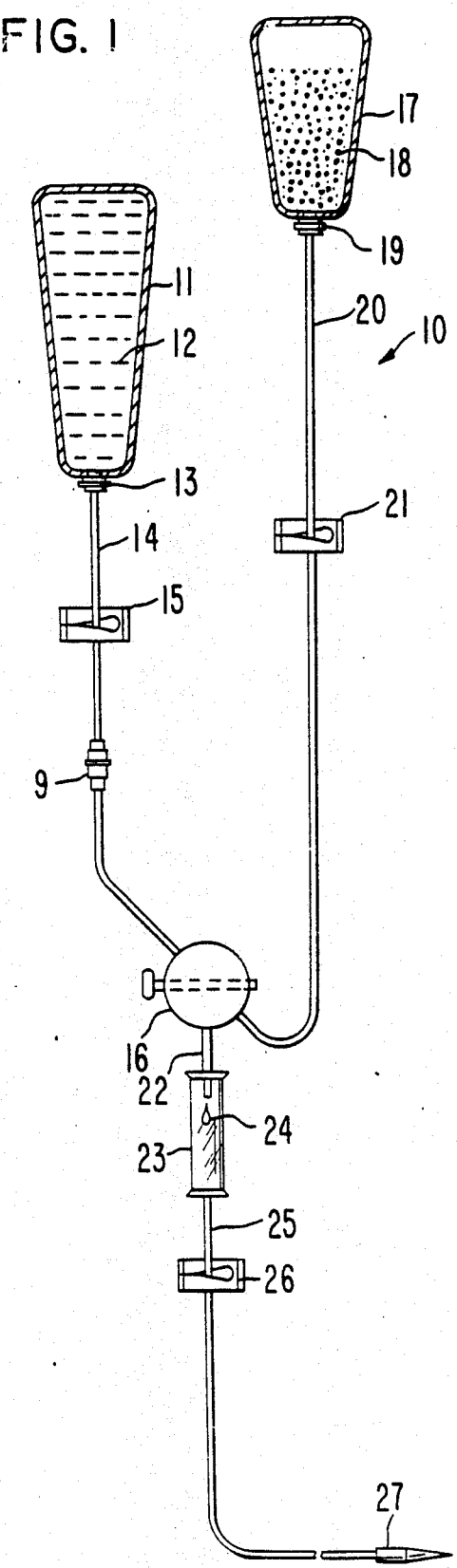
FIG. 1 is a perspective view of an intravenous delivery system provided by the invention comprising a first container of a medical fluid and a second container of drug initially free of medical fluid, with the first container and the second container in communication through a common valve.

FIG. 1 represents an intravenous delivery system provided by the invention and designated by the numeral 10. System 10 comprises a first or fluid container 11 that contains a medical fluid 12 acceptable for intravenous administration. Container 11, in the embodiment illustrated in FIG. 1, is made of plastic, preferably a flexible, transparent nontoxic plastic. In the embodiment illustrated, container 11 is shaped like a bag, and it is formed from a nontoxic poly(olefin), poly(vinyl chloride), or the like. In another embodiment, container 11 can be made of glass and it has the shape of a conventional intravenous glass container. Container 11 manufactured from plastic or glass is in a presently preferred embodiment a large volume container. Container 11, in the embodiment illustrated, represents a nonvented container containing medical fluid 12, which container is at atmospheric pressure, and collapses as it empties of medical fluid 12.

Container 11 is connected to the rest of intravenous delivery set 10 through an adaptor 13 that is suitably connected to the bottom of container 11. Adaptor 13 is hollow and it is optionally integrally formed, or it is suitably connected to container 11. Adaptor 13 is a means for conveying medical fluid 12 from container 11 to the rest of delivery system 10. The other end of adaptor means 13 is connected to a first section of medical grade tubing 14. Tube 14 passes through a fluid regulating clamp 15 used for adjusting the rate of fluid 12 flow from container 11 and through delivery system 10. Tube 14 optionally is provided with a one-way valve 9, typically of the duck-bill type, used to prevent solution from backing up into container 11. The other end of tube 14 is connected to means 16 for Permitting the passage and the conveyance of medical fluid 12 to other sections of delivery system 10, or for letting medical fluid 12 flow directly to a patient. In FIG. 1, means 16 is manufactured as a three-way valve.

Intravenous delivery system 10 comprises also a second or drug container 17. Container 17, in the embodiment illustrated, initially is essentially fluid-free and it initially contains drug 18. Container 17, in the embodiment illustrated is made of plastic, preferably a flexible transparent nontoxic plastic. In the embodiment illustrated, container 11 is shaped like an intravenous bag, and it is formed from a nontoxic poly(olefin), poly(vinyl chloride), and the like. In another embodiment, container 17 can be made from glass and it has the shape of a conventional intravenous glass container. Container 17 manufactured from plastic or glass is in a presently preferred embodiment a small volume container. Container 17, in the embodiment illustrated is nonvented, and container 17, after receiving an incoming fluid, collapses as it empties over time.

Container 17 is connected to the rest of intravenous delivery set 10 through adaptor means 19. Adaptor means 19 is connected to the bottom of container 17. Adaptor 19 is hollow and it is optionally integrally formed, or it is suitably connected to container 17. Adaptor 19 is a means for introducing fluid into container 17 and it is a means for permitting fluid to flow from container 17. The other end of adaptor means 19 is connected to a second section of medical tubing 20. Tubing 20 passes through a fluid regulating clamp 21 used for governing the rate of fluid flowing from container 17. The other end of tube 20 is connected to means 16, presently manufactured as a three-way valve.

A third section of medical grade tubing 22 releasably connected to means 16 is a fluid path for the passage of fluid from valve means 16 to a drip chamber 23. Drip chamber 23 is used to trap air and it also permits, in cooperation with regulator clamp 15, regulator clamp 16 and regulator clamp 26 adjustment of the rate of fluid flow through delivery system 10, as the flow proceeds dropwise 24. An outlet of drip chamber 23 is connected to one end of a third section of medical tube 25 that passes through a regulator clamp 26. Regulator clamp 26 is used for adjusting the internal diameter of tube 25 to regulate fluid flow in cooperation with sight drip chamber 23. The other end of medical tube 25 is connected to an adapter needle assembly 27 that is inserted, for example, into the vein of a warm-blooded animal.

Three-way valve means 16, as seen in FIG. 1, in one position permits the passage of medical fluid 12 to flow from container 11 directly into drip chamber 23, and hence into tube 25 through needle assembly 27 and into a patient, while concomitantly stopping fluid flow in tube 20 by clamp 21. In a second position, valve 16 allows fluid 12 to flow from container 17 into tube 20 and into container 17 when container 17 is lowered to a position lower than container 11. In a third position, valve 16 allows fluid 12 containing drug 18 to flow through tube 20 into drip chamber 23 and hence into tube 25 and through needle assembly 27 for administering drug 18 to a patient. Additional operating details of system 10 are presented later in this disclosure.

Figure 2:
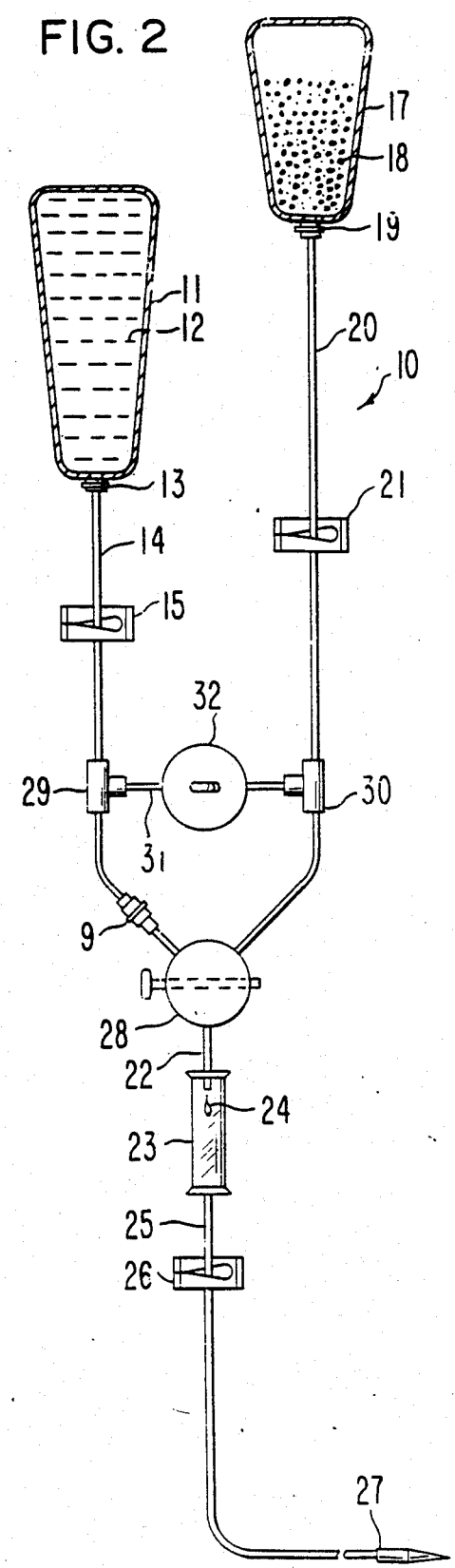
FIG. 2 is a perspective view of an intravenous delivery system provided by the invention comprising a first container of a medical fluid and a second container of drug initially free of medical fluid, with the first container and the second container in communication through a by-pass line.

Referring now to FIG. 2, there is illustrated an intravenous delivery system 10 similar to the intravenous delivery system 10 as seen in FIG. 1. In FIG. 2, delivery system 10 is provided with a two-way fluid-flow valve 28 that permits fluid 12 to flow from container 11 to needle assembly 27, or valve 28 can be set for permitting a drug solution formed in situ in container 17 to flow into needle assembly 27. FIG. 2 optionally is provided with a one-way valve 9 that can be used in cooperation with valve 28. Valve 28 also has an optional non-flow position for preventing fluid flow in tube 14 and tube 20. In FIG. 2, delivery system 10 additionally is provided with a bypass means for conveying fluid 12 from container 11 to drug container 17. The bypass means consist of a first T-couple 29 on tube 14, a second couple 30, which couples are suitably united by a connecting tube 31. Tube 31 is equipped with a bypass valve 32 that permits fluid to flow from container 11 into container 17. Thus, as seen in FIG. 2, an empty container 17 containing drug 18, in operation, would be lowered to a position below the position of container 11, bypass valve 32 would be opened, permitting fluid to flow from large volume container 11 into small volume container 17. When the small volume container 17 is filled with the desired amount of incoming fluid 12, thereby forming a drug 18 solution in situ in container 17, valve 32 is closed. Then, container 17 is raised from the lower position to a higher position, preferably higher than container 11. The contents of container 17 will thereafter be preferentially delivered through opened valve 28 into needle assembly 27 for administering drug 18 solution to a needy patient.

Figure 3:
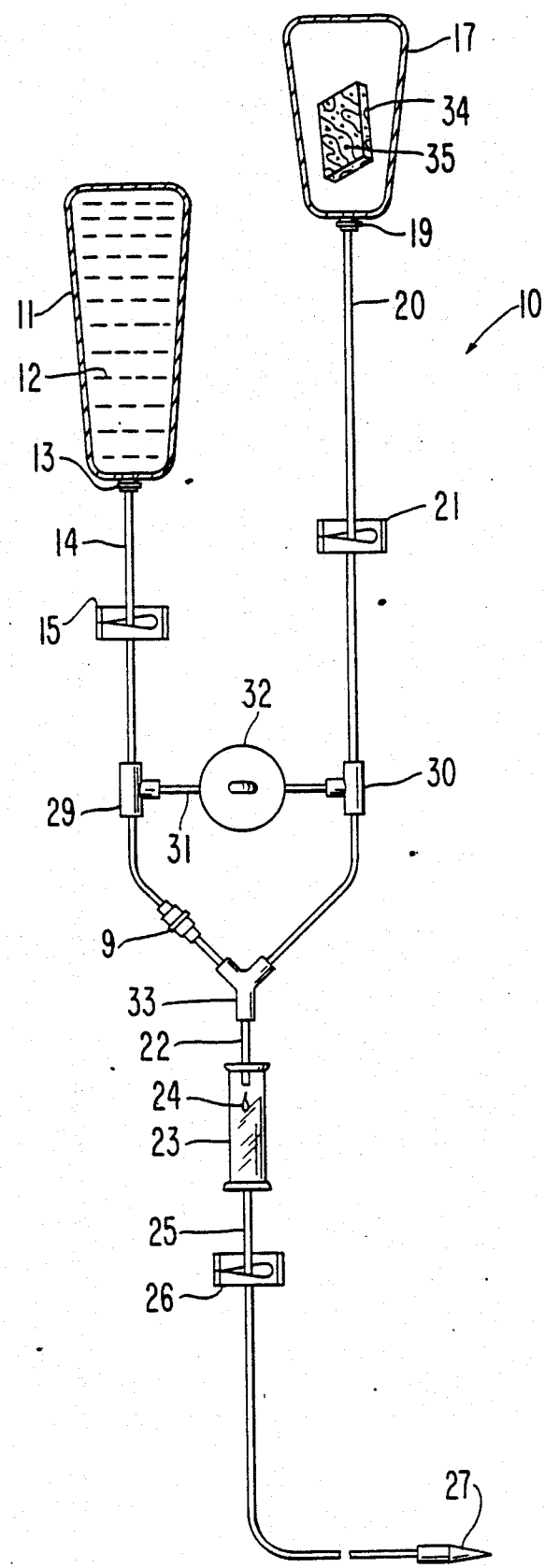
FIG. 3 is a perspective view of the intravenous delivery system illustrated in FIG. 2, with the second container housing a drug delivery device for releasing drug into the second container.

Referring now to FIG. 3, there is illustrated an intravenous delivery system 10 similar to delivery system 10 as seen in FIG. 1 and FIG. 2. In FIG. 3, delivery system 10 is provided with means 33, a branch coupler that can be made as a Y-type couple for receiving incoming tube 14, tube 20 and tube 22. Means 33 permits fluid flow in tube 14, tube 20 and in tube 22 to be correspondingly adjusted via flow regulator 15, flow regulator 21 and flow regulator 26. Further in FIG. 3, small volume container 17 is seen housing means 34 containing drug 35 for automatically constituting a beneficial drug solution in container 17 with medical fluid admitted into container 17. Originally, container 17 does not contain any medical fluid. Means 34, manufactured as a beneficial drug delivery device containing drug 35, releases drug 35 to fluid 12 that subsequently enters container 17. Means 34 releases a therapeutically effective amount of drug to form in container 17 a beneficial drug solution for administering to a patient.

Figure 4:
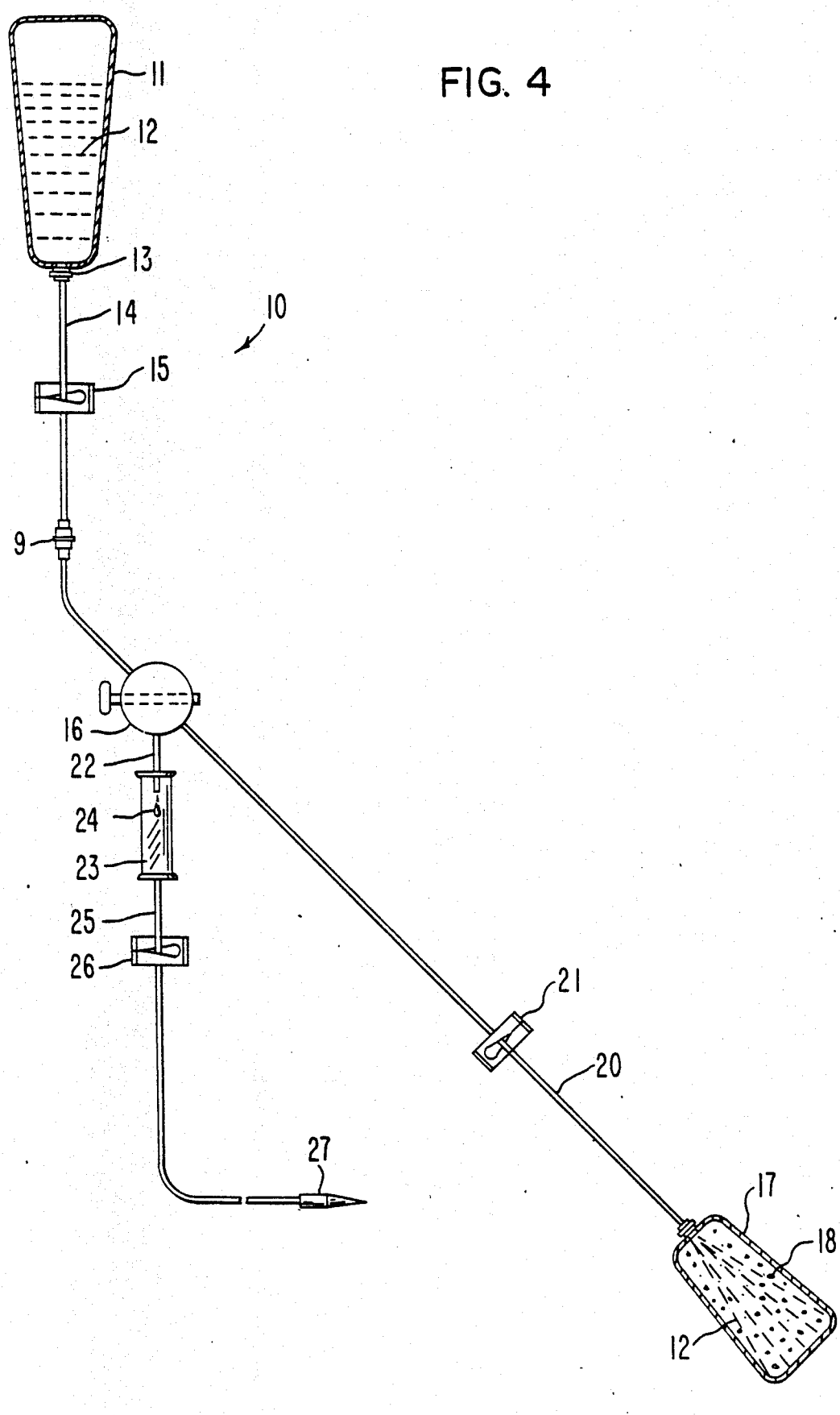
FIG. 4 is a view of the intravenous delivery system depicted in FIG. 1, with the delivery system in fluid transfer position illustrating the second container receiving fluid from the first container.
Figure 5:
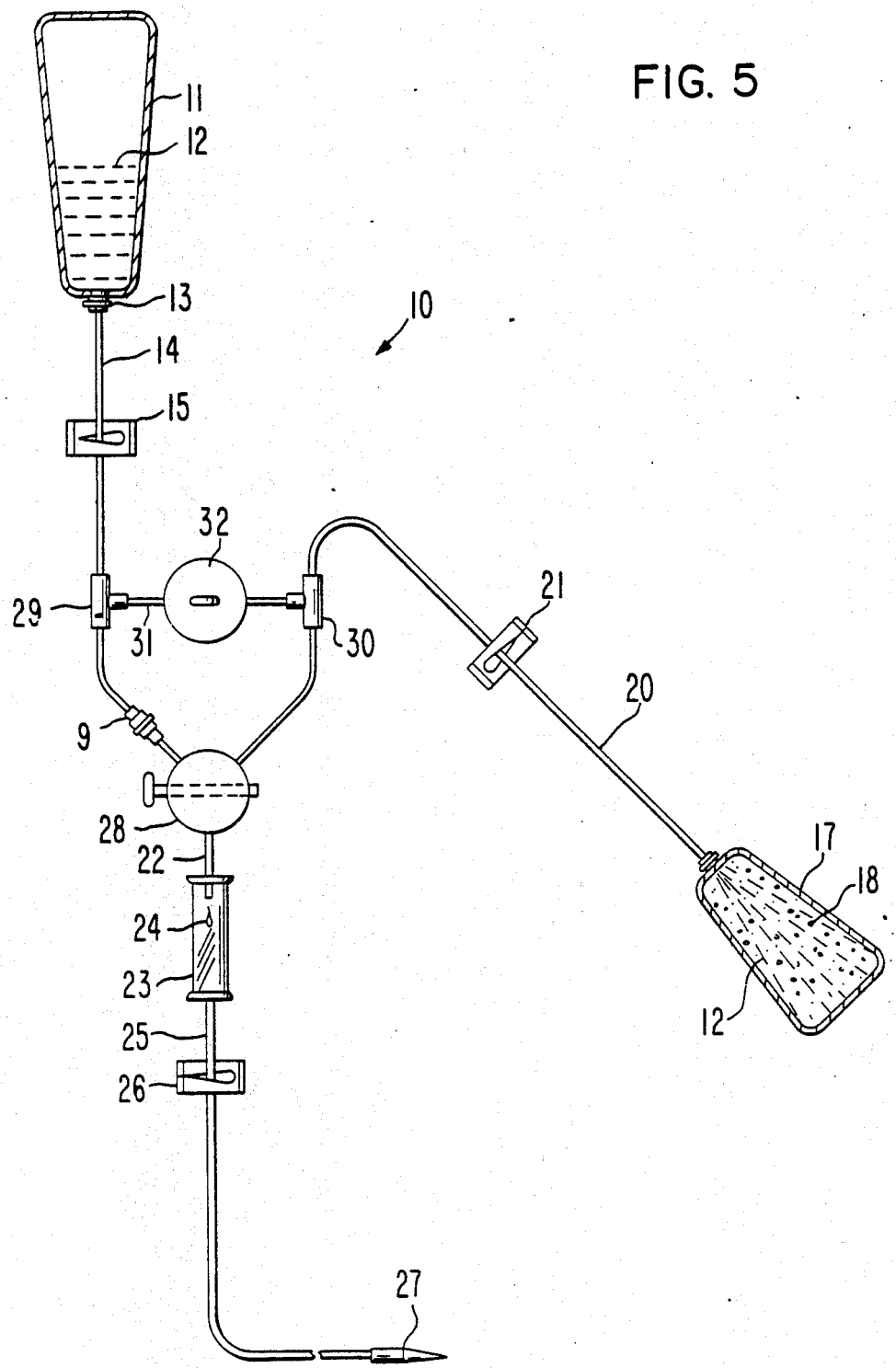
FIG. 5 is a view of the intravenous delivery system of FIG. 2, depicting the second container receiving medical fluid through the fluid bypass from the first container.
Figure 6:
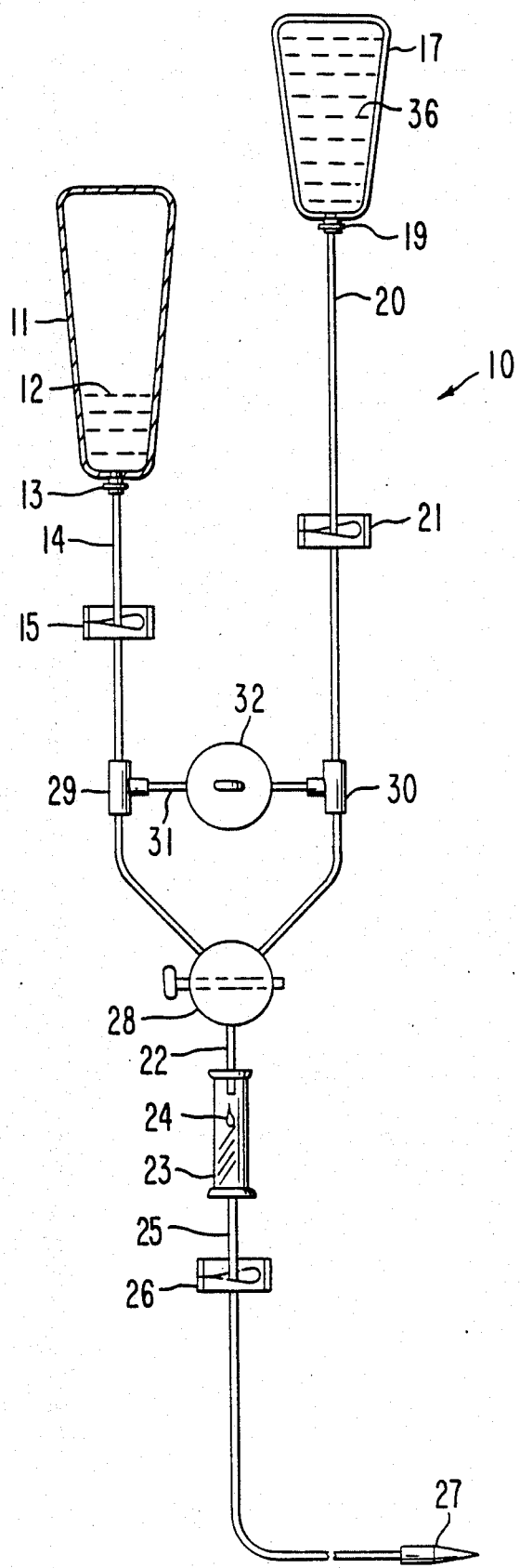
FIG. 6 is a view of an intravenous delivery system provided by the invention in position for delivering a fluid drug formulation to a recipient.

Referring now to FIG. 4, FIG. 5 and FIG. 6, intravenous delivery system 10 is seen in operation preparing a drug solution acceptable for intravenous administration. In FIG. 4 and in FIG. 5, a drug is added to an intravenously administrable fluid 12. In FIG. 4 and in FIG. 5, fluid is added to container 17 by gravity flow. This procedure is performed by lowering container 17 that initially contains a drug, or a dosage unit amount of drug for executing a therapeutic program, to a lower position than the higher position occupied by fluid container 11. In an embodiment not shown both container 11 and container 17 can have a volumetric scale thereon for indicating the volume of fluid in container 11 and for indicating the volume of fluid transferred into container 17. When container 17 has been filled with the desired volume of fluid, container 17 is raised from the lower position, as seen in FIG. 4 and in FIG. 5, to the higher position as seen in FIG. 6. The drug solution 36 formed in container 17 by drug 18 dissolving in fluid 12, is then administered to the patient. In additional operations, the contents of container 17 will be administered through needle assembly 27 until the level of fluid in the tube leading from container 17 falls to the same level as the fluid in container 11. When it is desired to provide another dose of fluid drug formulation from container 17, container 17 is moved to its lower position and a volume of fluid required to provide the drug solution is allowed to flow into container 17 from container 11. Then, the above described administration procedure is repeated for the desired therapy. Container 17 also can be allowed to administer all of its drug solution and remain empty of fluid until the next time drug is indicated for administration. The above procedure then is repeated for forming and administering the drug solution. The same procedures are used when container 17 contains a drug delivery device.

Medical fluid 12, as used herein, is typically a sterile solution, such as a solution of dextrose, a solution of an electrolyte, or saline. Medical fluid 12 also is a pharmaceutical vehicle, or a pharmaceutically acceptable carrier for beneficial drug 18 for forming a fluid drug formulation 35 that is to be administered to a recipient. The initial volume of medical fluid 12 in large volume container 11 is a volume sufficient for performing a therapeutic program, usually 500 ml to 1000 ml. Container 17, a small volume container, will generally have a capacity of 250 ml to 500 ml. It is understood, containers of other capacities likewise can be used for the present purpose.

The beneficial drug 18 initially present in container 17 is in any pharmaceutical state that forms a drug formulation solution with medical fluid 12 that enters container 17. The use of drug 18 in container 17 does not require any reconstituting, or admixture prior to use. The pharmaceutically acceptable form of drug, in a presently preferred embodiment, is solid. For the purpose of this invention, the term solid includes crystalline, microcrystalline, particle, pellet, granule, powder, tablet, dry, spray-dried, lyophilized, compressed powder, compressed granule, friable layers, forms that disintegrate and/or dissolve in the presence of incoming medical fluid, and the like. Container 17 generally contains an amount of beneficial drug for executing a prescribed therapeutic program, that is, an amount of drug for the preprogrammed delivery of a therapeutically effective amount of drug to a recipient to produce the desired beneficial therapeutic effect. Generally, the contianer will house from 1 mg to 25 g of drug, or more.

The delivery device containing drug as initially housed in container 17 are those that release drug by dissolution, diffusion, osmotic mechanism, or by other physical-chemical mechanism that produce a drug formulation. Representative drug delivery systems are the osmotic powered dispensing device disclosed by Theeuwes in U.S. Pat. No. 3,760,984; the osmotic dispensing device as disclosed by Theeuwes et al. in U.S. Pat. No. 3,916,899; the diffusion powered device a disclosed by Zaffaroni in U.S. Pat. No. 3,993,072., the osmotic miniature pump as disclosed by Higuchi in U.S. Pat. No. 3,995,631; the dispensing devices made from poly(orthoesters) and poly(orthocarbonates) as disclosed by Choi et al. in U.S. Pat. No. 4,138,344, dispensing devices made from a poly(ester), a poly(lactic), or a poly(glycolic) acid as disclosed by Ramwell in U.S. Pat. No. 3,888,975, and the like. The terms host and recipient as used herein denote animals, including warmblooded animals, which expression includes humans.

Figure 7:
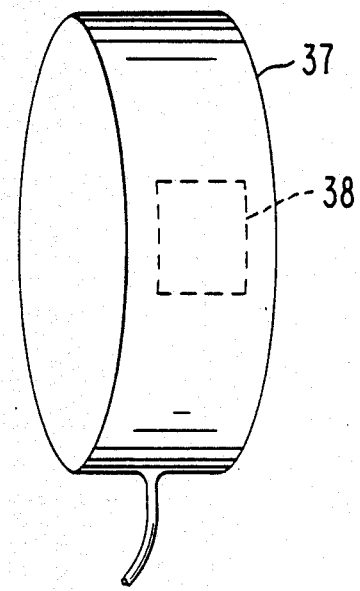
FIG. 7 and FIG. 8 are views of a container provided with a dispensing pouch containing drug for discharging drug into the container.
Figure 8:
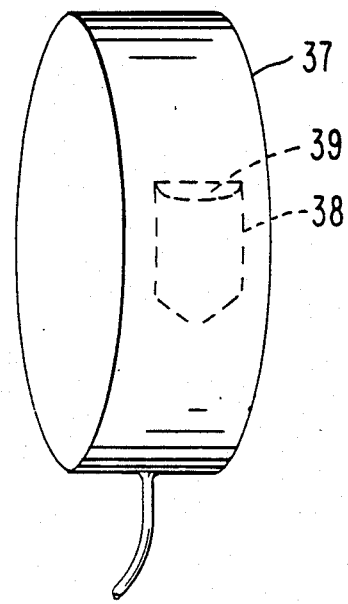
Figure 9:
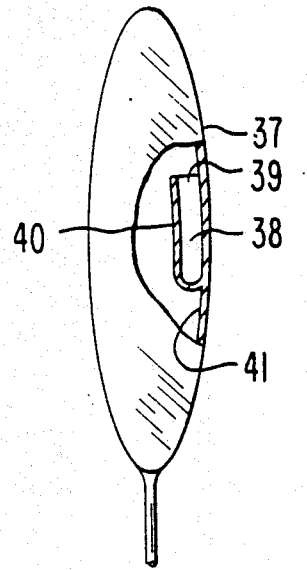
FIG. 9 is an opened view of the container of FIG. 7 and FIG. 8 depicting the dispensing pouch in a side view, and, FIG. 10 is an opened, side view of the container of FIGS. 7 and 8 depicting another dispensing pouch provided by the invention.
Figure 10:
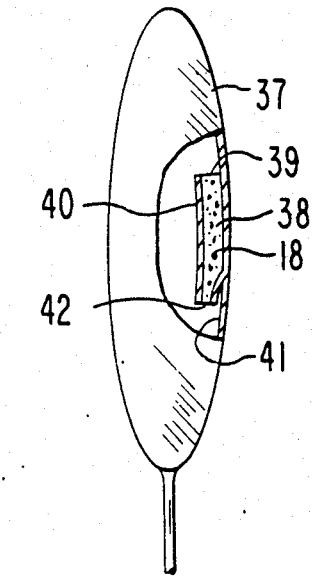

FIG. 7, FIG. 8, FIG. 9 and FIG. 10 illustrate additional embodiment of the invention for providing a drug for mixing with a medical fluid. The embodiment illustrated in FIG. 7 comprises a small volume container 37 provided with a pulse dosage dispenser 38 seen in dash-lines. Pulse dispenser 38, in one manufacture is made as a raised pouch, as illustrated in FIG. 8 in dash-lines. The pulse dispenser 38, made as a raised pouch is similar to a marsupial pouch. In this manufacture, the pouch is on the inside wall of container 37. The pouch contains drug and it serves to discharge a part of its drug through opening 39 into container 37 each time container 37 is lowered and inverted for receiving an incoming medical fluid. It is presently desired to keep the size of opening 39 small in order to minimize the amount of active drug released into container 37, and for keeping drug in reserve in pouch 38 for later use. In this manufacture pouch 38 functions as a pulse dosage dispenser, and acts as a reservoir of drug. Container 37 is used like container 17 with intravenous delivery system 10. FIG. 9 is a side view in opened section of the pouch as depicted in FIG. 7 and 8. The pouch is formed by a wall 40 made of a flexible polymeric material defining a pocket-like structure bonded around its edges to the inside surface 41 of container 37. The edges and the inside surface are bonded to each other by adhesive or solvent bonding or by any other suitable means to provide a fluid tight seal. This permits drug to be maintained in pouch 38 and it permits discharge only through opening 39 specifically provided for that function. FIG. 10 is similar to FIG. 9 with the added embodiment of a dispensing passageway 42 integrally formed in the bottom of the pouch and positioned distant from opening 39. FIG. 10 operates as previously described and it contains a medicament that can be added to an incoming fluid for intravenous use.

The novel and unobvious invention uses means for obtaining the precise control of drug delivery in an intravenous delivery system. While there has been described and pointed out features of the invention as applied to presently preferred embodiments, those skilled in the art will appreciate that various modifications, changes, additions and omissions in the delivery system illustrated and described can be made without departing from the spirit of the invention.

I claim:

1. A method for administering a drug formulation to a warm-blooded animal, wherein the method comprises:
   (a) admitting intravenously into an animal in need of a drug formulation a delivery member connected to an intravenously therapeutic delivery system, the system comprising:
      (1) a first container housing an intravenously acceptable fluid;
      (2) a second container housing an intravenously acceptable drug, said second container having an internal pouch that houses said drug, said pouch having fluid impermeable sidewalls, a fluid impermeable bottom wall and an upwardly facing opening so that a drug in the pouch leaves the pouch solely via said upwardly facing opening when fluid is introduced into said second container;
      (3) means for conveying fluid from the first container into the second container;
   (b) conveying fluid from the first container into the second container by moving at last one of said containers to a position whereby the second container is lower than the first container;
   (c) letting fluid from the first container into the second container for contacting the drug, thereby forming in situ a drug formulation acceptable for intravenous administration; and,
   (d) administering the drug formulation to the warm-blooded animal in a therapeutically effective amount by positioning the second container above the first container to permit drug formulation to flow from the second container to the delivery member for administering to said animal.

2. A method for administering a drug formulation to a warm-blooded animal, wherein the method comprises:
   (a) admitting intravenously into an animal in need of a drug formulation a delivery member connected to an intravenously therapeutic delivery system, the system comprising:
      (1) a first container housing an intravenously acceptable fluid;
      (2) a second non-vented container of one piece construction housing a dosage form comprising a drug that is released by the dosage form into fluid that enters the second container and contacts the dosage form, said second container initially free of intravenously acceptable fluid and initially being located above the first container;
      (3) means for conveying fluid from the first container into the second container;
   (b) conveying fluid from the first container into the second container by moving at least one of said containers to a position whereby the second container is lower than the first container;
   (c) letting fluid from the first container into the second container for contacting the dosage form causing it to release drug, thereby forming in situ a drug formulation acceptable for intravenous administration; and,
   (d) administering the drug formulation to the warm-blooded animal in a therapeutically effective amount by positioning the second container above the first container to permit drug formulation to flow from the second container to the delivery member for administering to said patient.

3. A method for administering a drug formulation to a warm-blooded animal, wherein the method comprises:
   (a) admitting intravenously into an animal in need of a drug formulation a delivery member connected to an intravenous therapeutic delivery system, the system comprising:
      (1) a first movable container housing an intravenously acceptable fluid;
      (2) a second non-vented movable container of one piece construction housing an intravenously acceptable dry drug and initially being located above the first container;
      (3) means for conveying fluid from the first movable container into the second movable container;
   (b) conveying fluid from the first movable container into the second movable container by moving at least one of said movable containers to a position whereby the second movable container is lower than the first movable container;
   (c) letting fluid from the first movable container into the second movable container for contacting and dissolving the drug, thereby forming in the formulation chamber a drug formulation acceptable for intravenous administration; and, (d) administering the drug formulation to the warm-blooded animal in a therapeutically effective amount by moving the second movable container housing the fluid drug formulation above the position of the first movable container to permit the fluid drug formulation to flow from the second container to the delivery member for administering to said animal.

4. An intravenous delivery system for forming a fluid drug formulation acceptable for intravenous administration, the delivery system comprising:
   (a) a first movable container comprising an intravenously acceptable medical fluid;
   (b) a second movable container housing an intravenously acceptable drug, said second container comprising an internal pouch that houses the drug, said pouch having fluid impermeable sidewalls, a fluid impermeable bottom wall and an upwardly facing opening so that a drug in the pouch leaves the pouch solely through the opening when fluid is introduced into the second container; and
   (c) means for conveying medical fluid from said first movable container into the second movable container for forming with the drug in the second container a fluid drug formulation acceptable for intravenous administration.

5. An intravenous delivery system for forming a fluid drug formulation acceptable for intravenous administration, the delivery system comprising:
   (a) a first movable container comprising an intravenously acceptable medical fluid;
   (b) a second non-vented movable container of one piece construction housing a dosage form comprising a drug that is released by the dosage form into fluid that enters the second container and contacts the dosage form, said second container initially free of medical fluid and initially being located above the first container; and,
   (c) means for conveying medical fluid from said first movable container into the second movable container for contacting the dosage form urging it to release drug and form in situ a fluid drug formulation acceptable for intravenous administration.

6. An intravenous delivery system for forming a fluid drug formulation acceptable for intravenous administration, the delivery system comprising:
   (a) a first movable container comprising an intravenously acceptable medical fluid;
   (b) a second non-vented movable container of one piece construction comprising an intravenously acceptable dry drug, said second movable container initially free of medical fluid and being positioned above the first movable container;
   (c) means for moving said second container into a position that is lower than the first container for letting fluid transfer from the first container into the second container for contacting the drug, thereby providing a fluid drug formulation acceptable for intravenous administration.

* * * * *